United States Patent [19]

Guss et al.

[11] 4,033,331
[45] July 5, 1977

[54] CARDIAC CATHETER AND METHOD OF USING SAME

[76] Inventors: Stephen B. Guss, 30 Jefferson Ave., Morristown, N.J. 07960; Mark R. Goldman, 1 Emerson Place No. 14A, Boston, Mass. 02114; Leonard M. Zir, 7 Elwin Road, Natick, Mass. 01760

[22] Filed: July 17, 1975

[21] Appl. No.: 596,644

[52] U.S. Cl. .............................. 128/2 M; 128/2 A; 128/2.05 R; 128/348; 128/DIG. 9
[51] Int. Cl.² .................................... A61M 25/00
[58] Field of Search ............ 128/2 A, 2 M, 2.05 R, 128/348, 349 R, 349 B, 350 R, 351, 343, DIG. 9

[56] References Cited
UNITED STATES PATENTS

| | | | |
|---|---|---|---|
| 1,596,754 | 8/1926 | Moschelle | 128/350 R |
| 2,688,329 | 9/1954 | Wallace | 128/349 R |
| 3,503,385 | 3/1970 | Stevens | 128/2 M |
| 3,605,725 | 9/1971 | Bentov | 128/2.05 R |

FOREIGN PATENTS OR APPLICATIONS 193,885  1/1965  Sweden .................. 128/DIG. 9

OTHER PUBLICATIONS

Cordis Ducor Phamphlet – 2d Edit. 1973 pp. 5, 8, 9, 12 & 16, relied on.

*Primary Examiner*—Dalton L. Truluck
*Attorney, Agent, or Firm*—Weingarten, Maxham & Schurgin

[57] ABSTRACT

A cardiac catheter being flexible throughout its length and having a deformable preformed distal end with a memory, that is, the distal end is formed with a set curvature to which the catheter tends to return when the deforming force is removed. A contour or stiffening wire slidably resides within a lumen separate from and parallel to the main fluid lumen of the catheter. The wire lumen is closed at the distal end of the catheter, the wire normally extending through substantially the full length of the wire lumen. The curvature of the preformed end of the catheter may be substantially reduced and the catheter straightened to some degree by extending the wire the full length of the catheter to the distal end thereof. The method of using the catheter employs the contour wire to create a plurality of different curvatures of the distal end of the catheter to aid in obtaining visual representations of different areas of the cardiac system.

8 Claims, 7 Drawing Figures

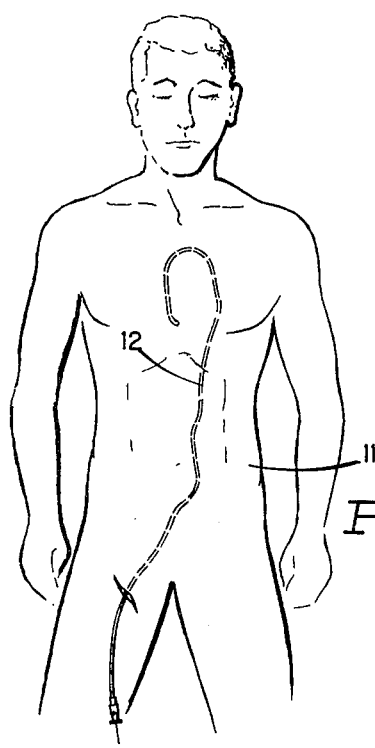
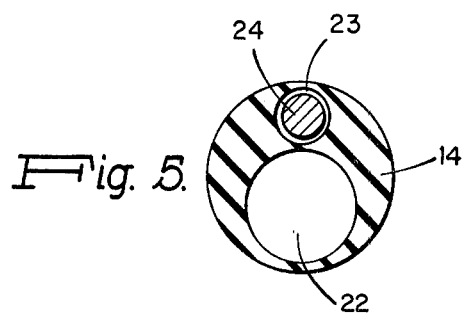
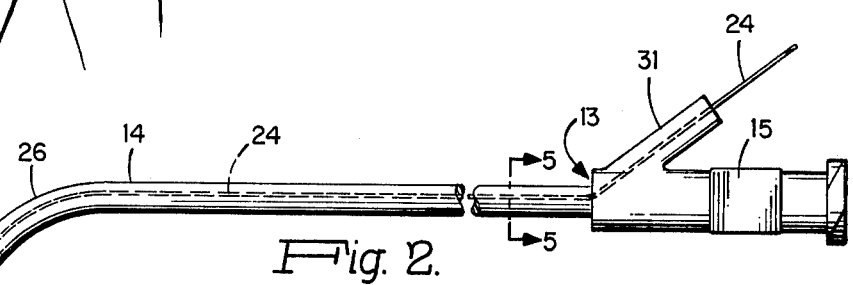
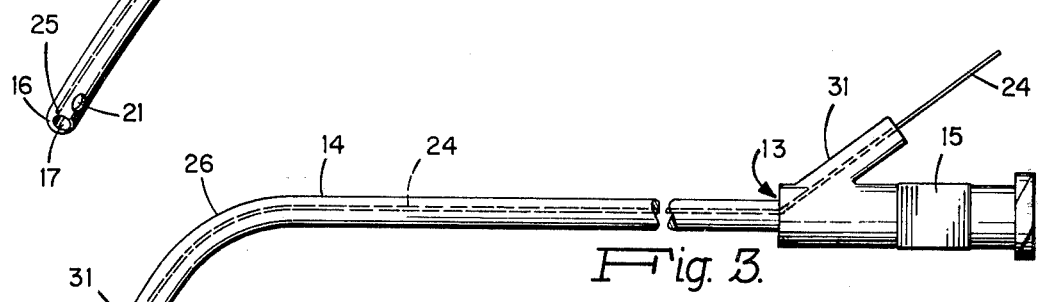
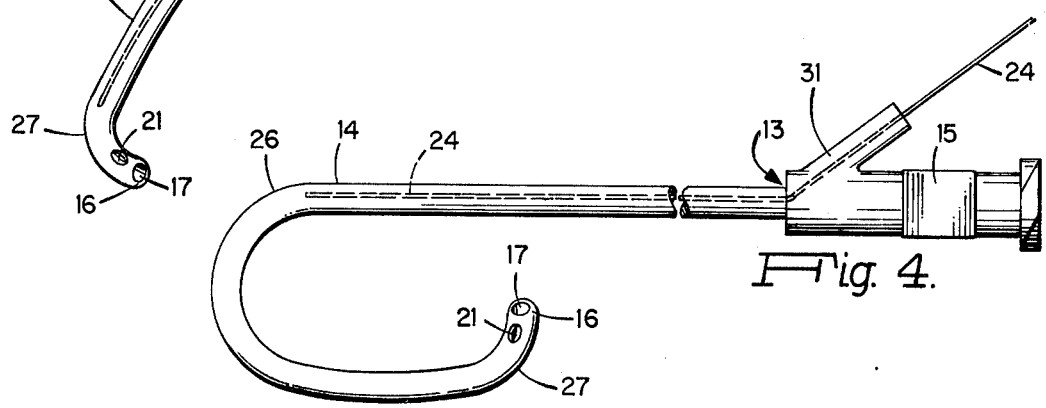

CARDIAC CATHETER AND METHOD OF USING SAME

FIELD OF THE INVENTION

This invention relates in general to cardiac catheters and more particularly concerns a single catheter having variable distal end curvatures which may be substituted for at least three conventional catheters.

DISCUSSION OF THE PRIOR ART

A standard set of procedures for determining possible defects in the various areas of the heart and the major blood vessels connected thereto requires that a radiopaque dye be injected into the proper area so that an x-ray or fluoroscope may be used to visually determine the anatomical characteristics of the area under study. The three more common areas of the cardiac system to which these procedures normally apply are the left coronary artery, the right coronary artery and the left ventricle. The manner in which dye has customarily been inserted for these procedures (often all three procedures are accomplished on a patient during a single period of time) is to form a cutaneous opening through the skin into the femoral artery in the upper thigh. A guide wire is then inserted through this artery and moved longitudinally through the aorta all the way to the heart itself. A special catheter used for inserting dye for study of the left coronary artery may then be slid over the wire and moved all the way to heart whereupon the wire is removed and the dye is injected through the lumen of the catheter. If another such procedure is to be accomplished immediately, the guide wire is again inserted throughout the entire length of the catheter, that catheter is removed and a second catheter, for study of, for example, the right coronary artery is inserted and the guide wire again removed. For study of the left ventricle, the guide wire is again inserted into the catheter already in the body, the right coronary catheter is removed, a catheter designed specifically for studying the left ventricle is inserted over the guide wire, the guide wire is removed and the dye is once again applied. Upon completion of this third aspect of the compound procedure, the third catheter is removed and the procedure is completed.

There are several patents which deal with cardiac catheters and one which appears to be pertinent to the present invention is Stevens U.S. Pat. No. 3,503,385. This patent discloses a catheter having a preformed deformable distal end for use in guiding the catheter around obstructions so that it follows the desired path. A central wire, extending axially through the main lumen of the Steven's catheter, is used for controlling the deformation of the distal end of the catheter and appears to remain in place while dye is being injected. Other patents which show different means for steering the end of a catheter are Burns et al U.S. Pat. No. 3,773,034 and Jeckel et al U.S. Pat. No. 3,528,406.

None of the prior art patents appear to disclose any means for diminishing the time and possible patient trauma involved in the complex procedures described above. Multiple insertions of guide wire and catheters can lead to thrombosis in that coagulation may commence along the guide wire surface and be forced into the heart when the catheter is slid over the guide wire. It is well known in the medical field that reduction of operative procedure time reduces the chances of complications which may adversely affect the patient. Accordingly, it is desirable to shorten the time involved for the type of procedure discussed above and to reduce chances of trauma from the standpoint of the patient, while also simplifying the procedures from the standpoint of the physician.

SUMMARY OF THE INVENTION

The cardiac catheter of this invention greatly simplifies dye insertion procedures and reduces the chances of adverse affects upon patients. This catheter is a single device which effectively takes the place of the three specifically different catheters described above. This catheter is made with a preformed, deformable distal end which can be straightened somewhat to facilitate insertion and is then permitted to assume part or all of its natural shape while in situ. The catheter is formed with two lumens throughout its length, a main lumen extending from the proximal through the distal end and a wire lumen, which is smaller than the main lumen and parallel thereto, extending from the proximal end to the distal end. The wire lumen is closed at the distal emd while the main lumen is open at both ends.

This catheter is preformed so that the distal end can assume the shapes necessary for the three procedures above described, one typical catheter shape being more curved than another. Upon the insertion, the contour wire resides in the wire lumen and extends throughout the entire length of the catheter, causing it to be comparatively straight and useful for one procedure. For another procedure, the wire is then pulled back from the distal end an inch or less and the distal end of the catheter asumes a further predetermined curvature. For a third procedure, the wire is removed a total of approximately two inches from the vicinity of the distal end whereupon the catheter assumes a further curvature because of its pre-set contour memory.

The trauma to the patient involved in using the catheter of the present invention is greatly diminished because the guide wire is inserted only once and the catheter is inserted only once for the three above described procedures. The main lumen remains free, that is, no wire resides therein during any procedures so that changes of catheter curvature from one procedure to the next can be made quickly and effectively with a minimum of time and trauma to the patient. Upon completion of a set of such procedures, the catheter of this invenion is withdrawn. Thus, there has been only one wire insertion and one catheter insertion even though three normally independent and separate procedures have been accomplished. It is believed, as previously mentioned, that coagulation may on occasion occur on the surface of the guide wire and such material be forced into the heart when the catheter is slid over its length. It is also possible that coagulation could occur where a guide wire remains within the lumen of the catheter during the dye injection procedures, as is the case with some of the prior art patents. With the procedure used with this invention, the catheter is inserted over the guide wire only once and after that, during the entire set of procedures, there is no exposed wire within the body or the catheter, thereby decreasing thrombogenicity.

Some of the standard catheters having a particular curvature designed for a single dye injection procedure have only one hole at the tip of the distal end, while other specific purpose catheters have one or more side holes near the tip of the distal end. The catheter of the present invention not only has an axial hole at the tip but has at least two holes in the side of the catheter adjacent the tip of the distal end. This improves the speed and the thoroughness with which the radiopaque material is applied to the desired area.

BRIEF DESCRIPTION OF THE DRAWING

The features, objects and advantages of this invention will be more clearly perceived from the following detailed description when taken in conjunction with the accompanying drawing in which:

FIG. 1 is a schematic representation of a human body showing a cardiac catheter therein;

FIG. 2 shows one configuration of the catheter of this invention;

FIG. 3 shows another configuration of the catheter of this invention;

FIG. 4 shows a third configuration of the catheter of this invention;

FIG. 5 is a sectional view taken through cutting plane 5-5 of FIG. 2;

DESCRIPTION OF THE PREFERRED EMBODIMENT

Figure 7:
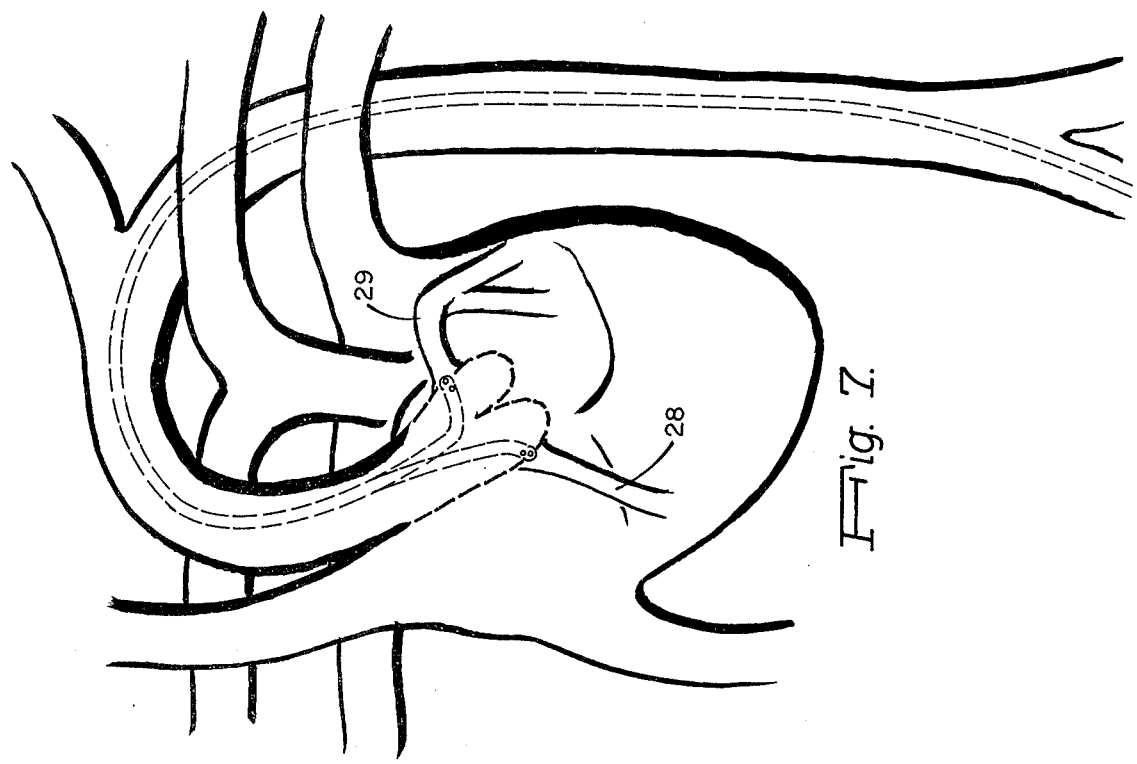
FIG. 7 shows the catheter of this invention in the aorta with the tip shown in alternative positions for purposes of obtaining coronary angiograms.

With the reference now to the drawing, FIG. 1 shows a patient 11 having a catheter 12 extending from a cutaneous opening into the femoral artery in the upper thigh into his heart. This indicates graphically but simply the problem associated with making visual inspection, such as by means of x-rays or fluoroscopies, of the cardiac system for diagnostic purposes.

Figure 6:
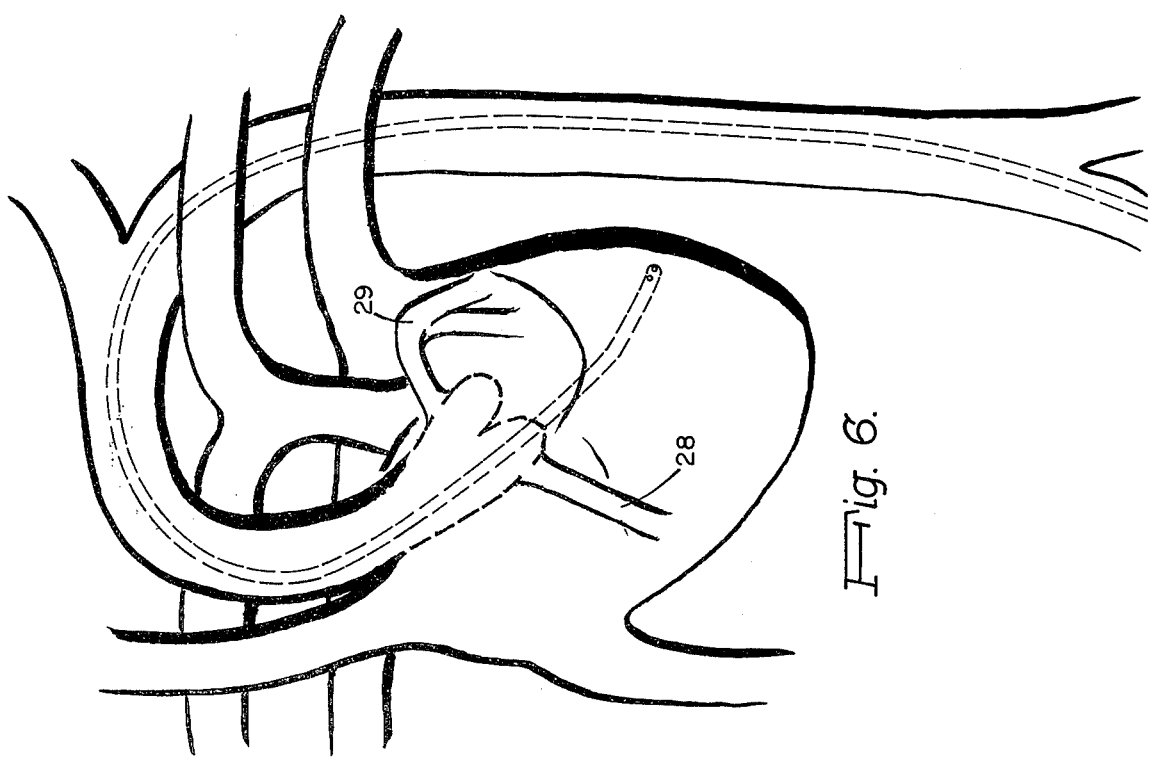
FIG. 6 is an enlarged view of a catheter inserted in the left ventricle for purposes of obtaining a left ventriculogram.

The catheter of this invention is shown in detail in FIGS. 2-5. The proximal end 13 of catheter 14 is fitted with a Luer-Lok (a registered trademark) 15 which is conventional for making connections with other fluid carrying tubular devices in the medical field. The distal end 16 has an axially opening 17 and preferably two side wall openings 21 spaced from but adjacent to distal end 16. As shown in FIG. 5, the catheter is formed with a main lumen 22 and a wire lumen 23 extending throughout the length of the catheter. The main lumen is open from proximal end 13 through opening 17 at the distal end while the wire lumen is open from proximal end 13 and is closed at distal end 16. A contour wire 24 resides within wire lumen 23 and normally extends throughout the length of the catheter to the closed distal end thereof at 25. As shown in FIG. 2, the catheter is as straight as it would normally be outside a patient but the distal end is sufficiently flexible that bend 26 will be substantially and easily straightened when inserted into the artery of the patient. The contour shown in FIG. 2 will be at least partially assumed when the catheter enters the heart and will naturally proceed through the aorta to the left ventricle for purposes of obtaining a left ventriculogram as shown in FIG. 6. Typically, a prior art catheter having a convoluted "pigtail" contour has been used for this procedure, but the less curved catheter shown in FIG. 2 has proven satisfactory.

In FIG. 3 the contour wire has been withdrawn a short distance, approximately one inch or less, and the catheter resumes a shape that was built in, that is, an additional relatively sharp contour 27 is formed. In this way, distal end 16 forms an angle with respect to that portion 31 of the catheter which is adjacent the distal end and between bends 26 and 27. This catheter is used for performing a coronary angiography (FIG. 7) of the right coronary artery 28 and accomplishes the same function as Judkins right coronary catheter.

With reference now to FIG. 4, the contour wire 24 has been withdrawn a total distance of approximately two inches from the distal end of the catheter and the catheter has now assumed its full curved shape between contour 26 and the distal end. This shape is used for performing a coronary angiography of the left coronary artery and accomplishes the same function as a Judkins left coronary catheter. It should be pointed out that the curvatures shown in FIGS. 2-4 occur with the catheter in a free state and they will be modified and straightened somewhat when acturally in use, due to the shape and confines of the cardiac system.

The method by which the catheter of the present invention is inserted into the patient follows standard procedure, that is, a guide wire is first inserted into the heart along the path as shown in FIG. 1 and the catheter is then inserted over the guide wire to the desired position. The guide wire is then removed and is not used again throughout the set of dye injections which are to be used with respect to that particular patent. After the ventriculogram is obtained, the catheter is withdrawn so the distal end resides in the aorta. The contour wire is withdrawn as shown in FIG. 3 and the catheter is rotated until the tip enters the right coronary artery 28 as shown in FIG. 7. After completion of this procedure, the catheter is then withdrawn from the aorta, the contour wire pulled back as shown in FIG. 4, and the catheter is slid forward until the tip enters the left coronary artery 29.

The connections to the catheter and the means by which the contour wire is moved are within present knowledge and do not form any part of the present invention. An example is shown in FIGS. 2-4 wherein connection 15 is formed with auxiliary fitting 31 through which contour wire 24 extends and is accessible for inserting and withdrawing. Since there is no fluid in the wire lumen, this fitting need not have any critical tolerances or seals. For purposes of example only, the outside diameter of the catheter is approximately 2.8 mm, the main lumen is approximately 2.3 mm in diameter and the wire lumen is approximately 0.4 mm in diameter. The catheter may be formed of any suitable surgical plastic materials such as plasticized vinyl resins, polyethylene, synthetic and natural rubbers and polyurethane elastomers, and usually includes a substance to make it radiopaque so that it can be readily seen by using a fluoroscope during the above-described medical procedures. The guide wire and contour wire may be any suitable surgical steel or other material which is medically non-reactive.

From the above description it is likely that those skilled in the art will be able to devise modifications and improvements which are within the scope of this invention.

What is claimed is:

1. A coronary catheter comprising:
   an elongated flexible tube having a main lumen extending throughout its length and open from the proximal end through the distal end, and having a smaller wire lumen extending from the proximal end to the distal end, the distal end of said wire lumen being closed, said main lumen and said wire lumen being parallel; and a freely longitudinally movable contour wire residing within said wire lumen of said tube;

a portion of said distal end of said tube being formed with a predetermined deformable curved contour with different degrees of curvature at different distances from said distal end, said distal end assuming one contour curve when said contour wire extends fully to the closed distal end of said wire lumen and assuming a plurality of different complex contour curves when said contour wire is longitudinally moved within said wire lumen to different locations with respect to said closed distal end thereof.

2. The coronary catheter recited in claim 1 wherein said distal end is formed with at least one hole through the side of said catheter to said main lumen adjacent to but spaced from the opening at the distal end of said main lumen.

3. The coronary catheter rcited in claim 1 and further comprising a Luer-Lok at said proximal end of said catheter.

4. The coronary catheter recited in claim 3 wherein said Luer-Lok is formed with an auxiliary branch fitting arranged at an angle with respect to the axis of said catheter through which said contour wire extends.

5. The coronary catheter recited in claim 1 wherein both said main lumen and said wire lumen are eccentric to the axis of said catheter.

6. A method for performing ventriculographies and coronary angiographies in a continuous set of procedures employing a flexible catheter having a deformable pre-set curvature at its distal end, a main fluid lumen, and a parallel wire lumen with a contour wire therein, said method being employed to obtain visual representations of the cardiac areas to be studied by such means as x-rays or fluoroscopes, said method comprising the steps of:

inserting a guide wire through an artery into a first area of a patient's heart;

inserting said catheter over said guide wire to the heart, said guide wire passing through said main lumen, said catheter having a first curvature at its distal end, said catheter having said contour wire extending throughout the length of said wire lumen;

removing said guide wire from said main lumen;

injecting radiopaque dye into said first area of the heart;

making a first visual representation of said first area;

withdrawing said contour wire a short distance to permit said catheter to assume a second curvature;

adjusting the distal end of said catheter to a second area of the patient's heart;

injecting radiopaque dye into said second area of the heart; and making a second visual representation of said second area.

7. The method recited in claim 6 and comprising the further steps of:

withdrawing said contour wire a further distance from said distal end of said catheter to permit said catheter to assume a third curvature;

adjusting the distal end of said catheter to a third area of the patient's heart;

injecting radioplaque dye into said third area of the heart; and making a third visual representation of said third area.

8. The method recited in claim 7 and comprising the further step of withdrawing said catheter from the patient.

* * * * *